(12) United States Patent
Otsuka et al.

(10) Patent No.: US 8,133,867 B2
(45) Date of Patent: Mar. 13, 2012

(54) METHOD FOR TREATING RHEUMATOID ARTHRITIS WITH AN ANTIBODY THAT BINDS TO A HEPATOCYTE GROWTH FACTOR RECEPTOR

(75) Inventors: Akira Otsuka, Higashiyamato (JP); Makoto Sakuma, Higashiyamato (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 109 days.

(21) Appl. No.: 12/293,541

(22) PCT Filed: Mar. 20, 2007

(86) PCT No.: PCT/JP2007/055654
§ 371 (c)(1), (2), (4) Date: Sep. 18, 2008

(87) PCT Pub. No.: WO2007/119447
PCT Pub. Date: Oct. 25, 2007

(65) Prior Publication Data
US 2009/0209733 A1 Aug. 20, 2009

(30) Foreign Application Priority Data
Mar. 20, 2006 (JP) .................................. 2006-077728

(51) Int. Cl.
*A61K 38/00* (2006.01)
*A61K 38/22* (2006.01)
*C07K 16/00* (2006.01)

(52) U.S. Cl. ..................... 514/16.6; 514/9.5; 530/387.1; 530/387.9

(58) Field of Classification Search ........................ None
See application file for complete search history.

(56) References Cited

U.S. PATENT DOCUMENTS

| | | | |
|---|---|---|---|
| 6,099,841 A * | 8/2000 | Hillan et al. ................ | 424/143.1 |
| 6,207,152 B1 * | 3/2001 | Schwall et al. ............. | 424/130.1 |
| 2002/0009432 A1 | 1/2002 | Iwamoto et al. | |
| 2003/0049644 A1 | 3/2003 | Rabin et al. | |
| 2003/0060515 A1 | 3/2003 | Sharpe et al. | |
| 2004/0121945 A1 * | 6/2004 | Liang et al. .................. | 514/12 |
| 2005/0054019 A1 * | 3/2005 | Michaud et al. ............. | 435/7.23 |
| 2005/0059688 A1 | 3/2005 | Moussy et al. | |

FOREIGN PATENT DOCUMENTS

| | | |
|---|---|---|
| WO | WO 94/06909 | 3/1994 |
| WO | WO 96/38557 | 12/1996 |
| WO | WO 98/00543 | 1/1998 |
| WO | WO 01/34650 | 5/2001 |
| WO | WO 01/44294 A2 * | 6/2001 |
| WO | WO 03/002108 | 1/2003 |
| WO | WO 2004/016597 | 2/2004 |
| WO | WO 2004/092154 | 10/2004 |

OTHER PUBLICATIONS

Furlong, 1992, BioEssays, vol. 14, issue 9, pp. 613-617.*
Koch, et al. "Hepatocyte Growth Factor. A Cytokine Mediating Endothelial Migration in Inflammatory Arthritis," *Arthhritis & Rheumatism.*, vol. 39, No. 9, pp. 1566-1575, 1996.
Nagashima, et al. "Hepatocyte Growth Factor (HGF), HGF Activator, and c-Met in Synovial Tissues in Rheumatoid Arthritis and Osteoarthritis," *The Journal of Rheumatology*, vol. 28, No. 8, pp. 1772-1778, 2001.
To, et al. "A Two-way Interaction Between Hepatocyte Growth Factor and Interleukin-6 in Tissue Invasion of Lung Cancer Cell Line," *Am. J. Respir. Cell. Mol. Biol.*, vol. 27, No. 2, pp. 220-226, 2002.
Yukioka, et al. "Levels of Hepatocyte Growth Factor in Synovial Fluid and Serum of Patients with Rheumatoid Arthritis and Release of Hepatocyte Growth Factor by Rheumatoid Synovial Fluid Cells," *The Journal of Rheumatology*, vol. 21, No. 12, pp. 2184-2189, 1994.
International Search Report dated Jul. 9, 2007.
Chan, et al. "Characterization of the Mouse *met* Proto-oncogene," *Oncogene*, vol. 2, pp. 593-599, 1988.
O'Donnell, et al. "Expression of Receptor Tyrosine Kinase Axl and its Ligand Gas6 in Rheumatoid Arthritis," *American Journal of Pathology*, vol. 154, No. 4, pp. 1171-1180, 1999.
Park, et al. "Sequence of *MET* Protooncogene cDNA has Features Characteristic of the Tyrosine Kinase Family of Growth-factor Receptors," *Proc. Natl. Acad. Sci.*, vol. 84, pp. 6379-6383, Sep. 1987.
Supplementary European Search Report issued to the corresponding European patent application and dated Dec. 17, 2009.
Wakitani, et al. "Hepatocyte Growth Factor Facilitates Cartilage Repair," *Acta Orthop Scand*, vol. 68, No. 5, pp. 474-480, 1997.

* cited by examiner

*Primary Examiner* — Robert Landsman
*Assistant Examiner* — Ian Dang
(74) *Attorney, Agent, or Firm* — Knobbe, Martens, Olson & Bear, LLP

(57) ABSTRACT

A therapeutic agent for rheumatoid arthritis, particularly a therapeutic agent for ameliorating an inflammatory symptom or bone deformity in rheumatoid arthritis, which comprises an antibody that binds to a hepatocyte growth factor receptor as an active ingredient.

9 Claims, 1 Drawing Sheet

METHOD FOR TREATING RHEUMATOID ARTHRITIS WITH AN ANTIBODY THAT BINDS TO A HEPATOCYTE GROWTH FACTOR RECEPTOR

TECHNICAL FIELD

The present invention relates to a novel therapeutic agent for rheumatoid arthritis.

BACKGROUND ART

First, abbreviations used in this application document are described as follows:
CIA: collagen-induced arthritis;
HGF: hepatocyte growth factor;
HGFR: hepatocyte growth factor receptor, HGF receptor; and
RA: rheumatoid arthritis.

RA is a disease which causes a nonspecific inflammation mainly in a synovial membrane of a joint, and produces a symptom of polyarthritis in the whole body. There are some prior arts relating to a treating agent for RA (refer to Patent Document 1 and Patent Document 2). However, RA is a complicated disease, and the treatment thereof has been limited to a symptomatic therapy. Thus, a novel therapeutic agent for RA has been desired.
Patent Document 1: JP-A-2002-187856
Patent Document 2: JP-A-2003-183177

DISCLOSURE OF THE INVENTION

The object of the present invention is to provide a novel therapeutic agent which is effective for RA.

The inventors of the present invention have intensively studied for solving the above object. As a result, they found that a novel and effective therapeutic agent for RA can be provided by using an antibody that binds to HGFR as an active ingredient. Thus, the present invention has been completed.

That is, the present invention provides a therapeutic agent for RA comprising an antibody that binds to HGFR as an active ingredient (hereinafter referred to as "therapeutic agent of the present invention").

The antibody that binds to HGFR preferably includes an antibody that specifically binds to HGFR. Further, the antibody that binds to HGFR is preferably an antibody capable of inhibiting the binding of HGF to HGFR (neutralizing antibody). Still further, an immunoglobulin class of the antibody that binds to HGFR is preferably IgG.

Still further, the therapeutic agent of the present invention is preferably used for ameliorating an inflammatory symptom. The inflammatory symptom is preferably an edema or a flare in limbs.

Still further, the therapeutic agent of the present invention is preferably used for ameliorating a bone deformity.

The present invention further relates to a method for treating RA that comprises administering the antibody that binds to HGFR.

The present invention also relates to use of the antibody that binds to HGFR in manufacturing an agent for treating RA.

BEST MODE FOR CARRYING OUT THE INVENTION

Figure 1:
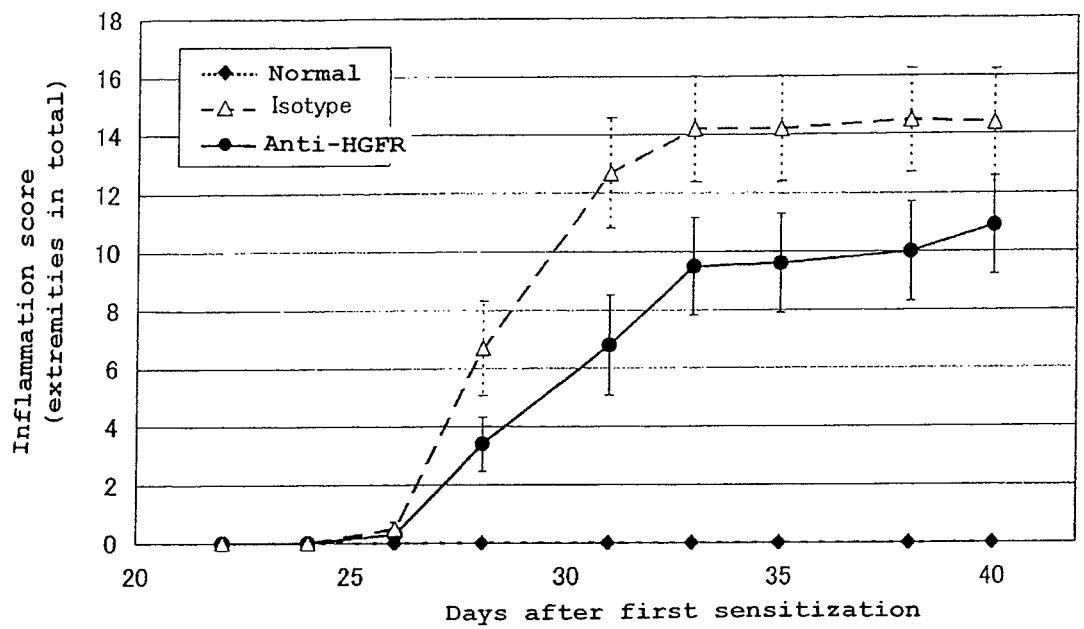
FIG. 1 is a graph showing inflammation score (CIA model) when an anti-HGFR antibody was administered.

Hereinafter, the present invention is described in detail by way of embodiments of the invention.

(1) Active Ingredient of the Therapeutic Agent of the Present Invention

A therapeutic agent of the present invention is a therapeutic agent for RA which comprises an antibody that binds to HGFR as an active ingredient.

The "antibody that binds to HGFR" used as an active ingredient of the therapeutic agent of the present invention is not particularly limited as long as the antibody binds to an HGFR molecule. It is preferable that the antibody specifically binds to HGFR.

Further, the animal species from which the antibody is derived is also not particularly limited, and it is preferable that the antibody is derived from mammals. Examples of the mammals include human, monkey, dog, cat, goat, sheep, horse, mouse, rat, guinea pig, rabbit, and pig.

Still further, the antibody may be a monoclonal antibody or a polyclonal antibody, but from viewpoints of ease of mass production, uniformity of quality, and the like, a monoclonal antibody is preferred.

The "antibody that binds to HGFR" can be obtained by a general antibody production method, in which HGFR or a portion thereof is used as an antigen. As "a portion of HGFR", an extracellular domain portion of HGFR is exemplified.

The method of obtaining an antigen is also not particularly limited. The antigen may be produced from a natural source by a known method or by a known chemical synthesis method of peptide (for example, a liquid phase synthesis method or a solid phase synthesis method, refer to "Fundamentals and Experiments of Peptide Synthesis" (1985), Nobuo Izumiya, Tetsuo Kato, Haruhiko Aoyagi, and Michinori Waki, published by Maruzen Co., Ltd.) based on an amino acid sequence of HGFR, which is already-known in itself, or a part of the sequence. Further, the antigen can be also produced by a genetic engineering method, in which a polynucleotide (DNA or RNA) corresponding to the amino acid sequence of the antigen is prepared, and then the polynucleotide is used.

For example, the sequence disclosed in Proc. Natl. Acad. Sci. U.S.A., 84, p 6379-6383 (1987) or the like can be used as an amino acid sequence or polynucleotide sequence of human-derived HGFR. Further, for example, the sequence disclosed in Oncogene, 2, p 593-599 (1988) or the like can be used as an amino acid sequence or polynucleotide sequence of mouse-derived HGFR. Still further, information on the extracellular domain portion is also disclosed in these documents.

The production of the antibody that binds to HGFR can be conducted, for example, as follows by using the above antigen, depending on which of the monoclonal antibody and the polyclonal antibody is to be produced.

For example, the monoclonal antibody can be produced by the method of Kohler and Milstein (Nature 256, 495-497 (1975)) by using the above antigen.

For example, the antigen is administered to an abdominal cavity, a subcutaneous part, a footpad, or the like of the animal to be immunized such as a mouse, a rat, a guinea pig, a rabbit, a goat, a sheep, a horse, a pig, a dog, a cat, and a domestic fowl. Then, a spleen cell, a lymphocyte, peripheral blood, or the like is collected from each of the immunized animals, and used for cell fusion with a myeloma cell which is a tumor cell line to thereby prepare a hybridoma. As the myeloma cell used for cell fusion, a cell line of each of various mammals can be utilized, but it is preferable to use a cell line derived from the animals belonging to the same kind as the animal to be immunized. Further, it is preferable to use a myeloma cell having a marker so that only the hybridoma grow while unfused myeloma cell is unable to survive, in order that unfused cell can be distinguished from fused cell after cell fusion. Still further, a line which does not secrete particular immunoglobulin is preferably used as a myeloma cell from a viewpoint that a target antibody can be readily obtained from a conditioned medium for a hybridoma.

The obtained hybridoma is continuously proliferated, and a hybridoma line which consecutively produces an antibody that specifically binds to the antigen is selected.

The thus selected hybridoma line is cultured in an appropriate medium, whereby a monoclonal antibody is obtained in the medium. Note that a monoclonal antibody may also be produced in a large amount by culturing the hybridoma line in vivo, such as an abdominal cavity of a mouse, and isolating from ascites or the like. The thus obtained monoclonal antibody may be purified by a general antibody purification method.

The polyclonal antibody can be produced as follows by using the above-described antigen.

In the similar way as the monoclonal antibody production method, the antigen is administered to the animal to be immunized.

At the time of immunizing the animal, it is desirable to use an adjuvant in combination, because the adjuvant activates an antibody-producing cell. Further, when an additional immunization is conducted by an ordinary method in the second or third week after the first immunization, antiserum having a high titer can be obtained. Blood is collected about a week after the final immunization, and serum is separated. The serum is subjected to a heat treatment thereby deactivating a complement, and after that, an immunoglobulin fraction is purified by a general antibody purification method.

Examples of the antibody purification method include: salting-out with sodium sulfate, ammonium sulfate, or the like; low temperature alcohol precipitation; selective precipitation fractionation by polyethylene glycol or isoelectric point; electrophoresis; ion exchange chromatography using an ion exchanger such as a diethylaminoethyl (DEAE)-derivative or carboxymethyl (CM)-derivative; affinity chromatography using protein A or protein G; hydroxyapatite chromatography; immunoadsorbent chromatography using immobilized antigen; gel filtration; and ultracentrifugation.

The antibody may be treated with a protease (e.g., plasmin, pepsin, papain, or the like) which does not decompose the antigen binding site (Fab) to be made into a fragment containing Fab or the like. Examples of the fragment containing Fab of an antibody include a Fabc fragment, a $(Fab')_2$ fragment, and the like in addition to the Fab fragment. These are also encompassed in the concept of "antibody" in this application document.

Further, when the monoclonal antibody is used as the antibody that binds to HGFR, the monoclonal antibody is not limited to that generated by the hybridoma, and may be a monoclonal antibody which is artificially modified for the purpose of lowering a heteroantigenicity against humans or the like. For example, as the monoclonal antibody that binds to HGFR, a chimeric antibody may be used, which consists of a variable region of an antibody derived from mammals other than human and a constant region of a human-derived antibody. The chimeric antibody can be produced by a known method using a genetic engineering method.

Further, a reconstructed humanized antibody may also be used. For example, the reconstructed humanized antibody can be obtained by replacing a complementarity-determining region of the human-derived antibody with a complementarity-determining region of the antibody derived from mammals other than human, by using a known genetic engineering method.

Whether or not an antibody binds to an antigen, or whether or not an antibody specifically binds to an antigen, can be easily determined by those skilled in the art by a known method using an antigen.

Still further, the immunoglobulin class of the antibody that binds to HGFR is also not particularly limited, but is preferably IgG.

Further, the "antibody that binds to HGFR" preferably includes an antibody that inhibits the binding of HGF to HGFR. The "antibody that binds to HGFR" inhibits the binding of HGF to HGFR preferably to a degree of 50% or less and more preferably to a degree of 10% or less, compared with the binding under the absence of the antibody. Such an antibody can be selected by a known method using HGF and HGFR, based on whether or not the binding therebetween is inhibited as an index.

Such an antibody may be produced by oneself in accordance with the above-mentioned method, or a commercially available product may also be used.

It is preferable that the "antibody that binds to HGFR" is highly purified so that it does not substantially contain contaminants that are not allowable for medicine.

By using the "antibody that binds to HGFR" as described above, the therapeutic agent for RA having an excellent pharmacological action can be produced.

(2) Administration Method, Etc., of the Therapeutic Agent of the Present Invention The therapeutic agent of the present invention can be used for the treatment of RA. In this application document, "RA" includes, not only RA defined under the strict definition of medical science, but also conditions that show symptoms which are the same as or similar to those of RA and are acknowledged as RA in this technical field.

The therapeutic agent of the present invention is not particularly limited in terms of a purpose of administration, a subject to be administered, an administration route, an administration method, a dosage form, a blending quantity of the active ingredient, a dose, an administration interval, and the like, as long as it is the therapeutic agent for RA comprising the above-mentioned antibody that binds to HGFR as an active ingredient.

The term "therapeutic agent for RA" used in this application document is not particularly limited as long as it is an agent used for some kind of treatment for RA. Therefore, each of the agents used for the purposes of prophylaxis, maintenance (prevention of deterioration), alleviation (symptom amelioration), and treatment of RA is included in the concept of the therapeutic agent of the present invention. That is, the present invention includes the concepts of a prophylactic agent, a maintenance agent (deterioration preventing agent), an alleviating agent (symptom-ameliorating agent), and a treating agent for RA.

Further, the therapeutic agent of the present invention exhibits a particularly excellent ameliorating action to an inflammatory symptom in RA. Therefore, the agent is preferably used for ameliorating the inflammatory symptom in RA. The inflammatory symptoms used herein are not particularly limited as long as they are symptoms caused by inflammation, but the inflammatory symptoms preferably include an edema and a flare in limbs.

In addition, the therapeutic agent of the present invention exhibits a particularly excellent ameliorating action to a bone deformity in RA. Therefore, it is preferably used for ameliorating the bone deformity in RA.

The subject animal to which the therapeutic agent of the present invention is administered is not particularly limited as long as the animal has a possibility of being affected by RA. Mammals are exemplified as such animals, and examples thereof include human, monkey, dog, cat, goat, sheep, horse, mouse, rat, guinea pig, rabbit, and pig. Of these, human is preferred. The therapeutic agent of the present invention is to contribute to the treatment of RA. Therefore, the agent can be applied to the animal under a condition of needing the treatment to RA.

The administration route of the therapeutic agent of the present invention is not particularly limited as long as an action of the therapeutic agent for RA is exhibited, and the therapeutic agent can be administered by injection (including intra-articular, intravenous, intramuscular, subcutaneous, intradermal, and intra abdominal injections) or by inhalation, or administered nasally, orally, or dermally, for example. The administration method for the therapeutic agent of the present invention can be appropriately selected, such as direct administration to a specific site by injection, depending on the desired site or the like.

Depending on the administration route and the administration method as described above, the antibody that binds to HGFR as an active ingredient is appropriately formulated into a pharmaceutical, whereby the therapeutic agent of the present invention is prepared.

Examples of the dosage form of the therapeutic agent of the present invention include injections (solutions, suspensions, emulsions, solid preparations for dissolution before use, etc.), tablets, capsules, liquid solutions, granules, powders, lipo-forming preparations, ointments, plasters, lotions, pastes, adhesive preparations, gels, suppositories, powders for external use, sprays, and inhalation powders. It is preferable that therapeutic agent of the present invention has a form of liquid solution such as injection.

The liquid solution can be produced by dissolving the antibody that binds to HGFR as an active ingredient in an appropriate aqueous solvent or a solvent which is commonly used in the medical field. Examples of the solvent include distilled water, buffer, saline, and water containing water-miscible organic solvent.

When the therapeutic agent of the present invention is provided as the injection, the form thereof may be any one of a solution, a frozen product, and a freeze-dried product. The therapeutic agent is filled into an appropriate container such as an ampule, a vial, a syringe for injection, or the like, and the container is sealed. The container is distributed as it is or stored, and the therapeutic agent can be administered as the injection.

A known method can be used for formulating the therapeutic agent of the present invention into a pharmaceutical. Further, in preparing the pharmaceutical, the following ingredients generally used in the medical field can be used, as long as the ingredients do not adversely affect the antibody that binds to HGFR and does not affect the effect of the present invention. The above ingredients include other pharmaceutical active ingredients (for example, an anti-inflammatory agent, an analgesic, a vitamin preparation, an antibacterial agent, a growth factor, and an adherence factor), a stabilizing agent, an emulsifying agent, an osmotic pressure adjusting agent, a pH adjusting agent, a buffering agent, a tonicity agent, a preservative, a soothing agent, a coloring agent, an excipient, a binder, a lubricant, a disintegrating agent, and the like.

The blending quantity of the antibody that binds to HGFR as an active ingredient, the dose per one administration, the administration interval, and the like of the therapeutic agent of the present invention can be determined depending on a kind of an active ingredient, a purpose of administration, a subject to be administered, an administration route, an administration method, a dosage form, specific symptom, age, sex, and weight of a patient, and the like. There is exemplified about 5 mg to 50 g per adult per administration.

Further, the therapeutic agent of the present invention may be administered only once, or may be administered a plurality of times. When the therapeutic agent is administered a plurality of times, it may be administered each and every day, or may be administered at an interval of about 1 to 7 days. Further, the therapeutic agent may be administered once a day, or may be administered twice to three times a day.

EXAMPLES

Hereinafter, the present invention is more specifically described by referring to examples.

1. Preparing Method of a Model Animal of RA (CIA Model)

A CIA model was prepared by sensitizing a 6 to 7-week-old DBA/1J male mouse (Charles River Laboratories Japan, Inc.) by intracutaneous injection at base of the tail of the mouse of 150 µg/0.1 ml emulsion obtained by mixing a bovine-derived type II collagen (3 mg/ml, dissolved in 0.01M acetic acid) with the same amount of a Freund's complete adjuvant, and then subjecting the mouse to an additional sensitization on the 21st day from the first sensitization. The method of the additional sensitization is similar to that of the first sensitization. It is known that the CIA model exhibits an inflammation in limbs on the 4th to 5th day from the additional sensitization, and the inflammation reaches its peak on the 10th to 20th day from the additional sensitization. The CIA model is widely utilized as a model of rheumatoid arthritis in human and as a tool for developing a therapeutic drug.

2. Pharmacological Test (1) The test in which the antibody that binds to HGFR was administered to the model animal was conducted, in order to examine whether the disease activity of the model animal is ameliorated by the antibody that binds to HGFR. The antibody which has an ability to inhibit the binding of HGF to HGFR (anti-mouse HGFR antibody, R&D SYSTEMS, catalog No. AF527) was used as the antibody. The antibody is a purified product of a polyclonal antibody obtained by using an extracellular domain portion of mouse-derived HGFR as an antigen. The antibody specifically binds to HGFR, and an immunoglobulin class thereof is IgG (hereinafter, the antibody is referred to as "anti-HGFR antibody").

The anti-HGFR antibody which was adjusted with saline to a final concentration of 2 mg/ml was used.

(2) The CIA Model Prepared by the Above Method was Used as an RA Model.

The anti-HGFR antibody was intraabdominally administered at 200 µg/0.1 ml/mouse (about 10 mg/kg weight) on the 24th, 27th, 30th, and 33rd days (four times in total) from the first sensitization (anti-HGFR group, n=10). On the other hand, for a control group with respect to the anti-HGFR antibody group, a normal goat IgG, which is an isotype control of the anti-HGFR antibody (Cappel, catalog No. 55926), was intraabdominally administered at 200 µg/0.1 ml/mouse (about 10 mg/kg weight) on the 24th, 27th, 30th, and 33rd days (four times in total) from the first sensitization (isotype group, n=10).

Further, a normal mouse of the same weekly age as the CIA model was used as a normal group, and intraabdominally administered with 0.1 ml of saline per mouse on the 24th, 27th, 30th, and 33rd days (four times in total) from the start of the test (n=3).

(3) The amelioration of arthritis was evaluated by inflammation score in limbs (fingers excluding thumbs, insteps, and heels of both feet and fingers excluding thumbs and dorsum manus of both hands (22 parts in total) were observed, whereby a part in which an edema or a flare was seen was given a score of 1 point, and accordingly, the maximum score was 22 points per mouse) (evaluation was conducted three times a week, after the additional sensitization).

The average value±standard deviation of inflammation score of each of the groups at each of the measured days was plotted on a graph. The results are shown in FIG. 1.

As a result, it was found that the inflammation score of the anti-HGFR group was improved as compared with that of the isotype group (negative control) (FIG. 1).

Figure 2:
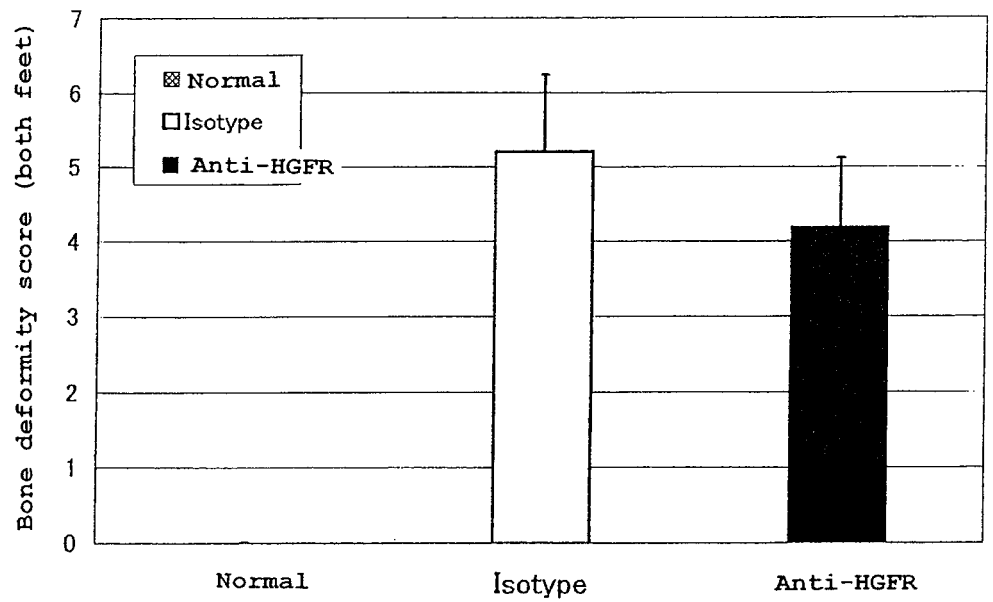
FIG. 2 is a graph showing bone deformity score (CIA model) when an anti-HGFR neutralizing antibody was administered.

(4) Further, radiographs of hind limbs of the mouse were taken on the 41st day of the first sensitization, to thereby observe a degree of bone deformity in four parts on the tarsal side, which were a tarsal bone, a talocalcaneal bone, a metatarsal bone, and a tibial bone. Depending on the degree of the bone deformity, the scores of 0 (no change), 1 (slight deformity), 2 (moderate deformity), and 3 (severe deformity) were given (the maximum score per mouse became 24 points) to evaluate the degree of bone deformity of the both hind limbs, and an average value±standard deviation of each of the groups was plotted on a graph. The results are shown in FIG. 2.

As a result, it was found that the bone deformity score of the anti-HGFR group was improved as compared with that of the control group (isotype group).

It was found from the results that the RA was ameliorated by the administration of the anti-HGFR antibody.

From the above results, it was found that an effective therapeutic agent for RA can be provided by using the antibody that binds to HGFR as an active ingredient.

INDUSTRIAL APPLICABILITY

According to the present invention, a novel and effective therapeutic agent for RA can be provided, and thus, the present invention is very useful.

The invention claimed is:

1. A method of treating rheumatoid arthritis, comprising administering an antibody that binds to a hepatocyte growth factor receptor to a subject in need thereof, wherein the antibody that binds to hepatocyte growth factor receptor is capable of inhibiting the binding of hepatocyte growth factor to hepatocyte growth factor receptor.

2. The method according to claim 1, wherein the antibody that binds to hepatocyte growth factor receptor has an ability to inhibit the binding of hepatocyte growth factor to hepatocyte growth factor receptor to a degree of 10% or less compared with the binding in the absence of the antibody.

3. The method according to claim 1, wherein an immunoglobulin class of the antibody that binds to a hepatocyte growth factor receptor is IgG.

4. A method of ameliorating an inflammatory symptom of rheumatoid arthritis, comprising administering an antibody that binds to a hepatocyte growth factor receptor to a subject in need thereof, wherein the antibody that binds to hepatocyte growth factor receptor is capable of inhibiting the binding of hepatocyte growth factor to hepatocyte growth factor receptor.

5. The method according to claim 4, wherein the inflammatory symptom is an edema or a flare in limbs.

6. A method of ameliorating a bone deformity in rheumatoid arthritis, comprising administering an antibody that binds to a hepatocyte growth factor receptor to a subject in need thereof, wherein the antibody that binds to hepatocyte growth factor receptor is capable of inhibiting the binding of hepatocyte growth factor to hepatocyte growth factor receptor.

7. A method of treating rheumatoid arthritis in a subject in need thereof, comprising administering to said subject an effective amount of a neutralizing antibody that binds to a hepatocyte growth factor receptor.

8. A method of ameliorating an inflammatory symptom of rheumatoid arthritis in a subject in need thereof, comprising administering to said subject an effective amount of a neutralizing antibody that binds to a hepatocyte growth factor receptor.

9. A method of ameliorating a bone deformity in rheumatoid arthritis in a subject in need thereof, comprising administering to said subject an effective amount of a neutralizing antibody that binds to a hepatocyte growth factor receptor.

* * * * *